United States Patent
Mohammed et al.

(10) Patent No.: US 11,007,366 B2
(45) Date of Patent: May 18, 2021

(54) STIMULATION DEVICE FOR ACTIVATING AT LEAST ONE MUSCLE INVOLVED IN RAISING THE FOOT

(71) Applicant: Universite Paris Est Creteil Val De Marne, Creteil (FR)

(72) Inventors: Samer Mohammed, Choisy-le-Roi (FR); Yacine Amirat, Thiais (FR); Jean-Michel Gracies, Paris (FR)

(73) Assignee: Universite Paris Est Creteil Val De Marne

( * ) Notice: Subject to any disclaimer, the term of this patent is extended or adjusted under 35 U.S.C. 154(b) by 125 days.

(21) Appl. No.: 16/335,481

(22) PCT Filed: Sep. 15, 2017

(86) PCT No.: PCT/EP2017/073235
§ 371 (c)(1),
(2) Date: Mar. 21, 2019

(87) PCT Pub. No.: WO2018/054764
PCT Pub. Date: Mar. 29, 2018

(65) Prior Publication Data
US 2019/0217091 A1    Jul. 18, 2019

(30) Foreign Application Priority Data

Sep. 22, 2016  (FR) ...................... 1658930

(51) Int. Cl.
*A61N 1/36* (2006.01)
*A61H 3/00* (2006.01)
(Continued)

(52) U.S. Cl.
CPC ........ *A61N 1/36003* (2013.01); *A61B 5/1071* (2013.01); *A61B 5/112* (2013.01);
(Continued)

(58) Field of Classification Search
CPC ..... A61B 5/1071; A61B 5/112; A61B 5/4836; A61F 5/01; A61H 3/00; A61N 1/0452; A61N 1/36003; A61N 1/3603
See application file for complete search history.

(56) References Cited

U.S. PATENT DOCUMENTS 4,569,352 A * 2/1986 Petrofsky ........... A61N 1/36003
607/49
4,711,242 A   12/1987 Petrofsky
(Continued)

OTHER PUBLICATIONS

French Search Report for Application No. FR 1658930 dated Jun. 20, 2017, 2 pages.
(Continued)

*Primary Examiner* — Jonathan T Kuo
(74) *Attorney, Agent, or Firm* — Lerner, David, Littenberg, Krumholz & Mentlik, LLP

(57) ABSTRACT

A stimulation device for activating at least one muscle involved in raising the foot while an individual is walking, comprising sensors which are to be placed on a lower limb of the individual, permitting calculation of a flexion angle of the knee; electrodes which are to be placed on the one or more muscles to be activated and able to electrically stimulate the one or more muscles, and a processing unit with computing means for calculating the value of the flexion angle of the knee on the basis of the measurement signals and for determining the oscillation phase in a walking cycle of the individual, and control means for the electrodes, the control means being designed to activate the electrodes only in the oscillation phase of a walking cycle of the individual, such that the electrodes generate an electrical stimulation with an intensity depending on the flexion angle of the knee, the intensity increasing as the flexion angle of the knee decreases, during the re-extension of the knee during the oscillation phase.

11 Claims, 10 Drawing Sheets

(51) Int. Cl.
    *A61B 5/11*     (2006.01)
    *A61N 1/04*     (2006.01)
    *A61B 5/107*     (2006.01)
    *A61B 5/00*     (2006.01)
    *A61F 5/01*     (2006.01)

(52) U.S. Cl.
    CPC ............. *A61B 5/4836* (2013.01); *A61H 3/00* (2013.01); *A61N 1/0452* (2013.01); *A61N 1/3603* (2017.08); *A61F 5/01* (2013.01)

(56) References Cited

U.S. PATENT DOCUMENTS

| | | | |
|---|---|---|---|
| 4,796,631 A | 1/1989 | Grigoryev | |
| 8,452,410 B2 * | 5/2013 | Emborg | A61N 1/36031 607/49 |
| 2008/0234782 A1 * | 9/2008 | Haugland | A61B 5/04001 607/48 |
| 2012/0059432 A1 * | 3/2012 | Emborg | A61N 1/36003 607/49 |
| 2016/0339240 A1 * | 11/2016 | Mihara | A61B 5/1038 |

OTHER PUBLICATIONS

International Search Report for PCT/EP2017/073235, dated Dec. 12, 2017.
O'Halloran, et al., "Modified Implanted Drop Foot Stimulator System with Graphical User Interface for Customised Stimulation Pulse-Width Profiles", Medical and Biological Engineering and Computing, vol. 41, No. 6, Nov. 2003, pp. 701-709.
Piazza and Delp, "The Influence of Muscles on Knee Flexion During the Swing Phase of Gait", Journal of Biomechanics, vol. 29, No. 6, Jun. 1996, pp. 723-733.

* cited by examiner

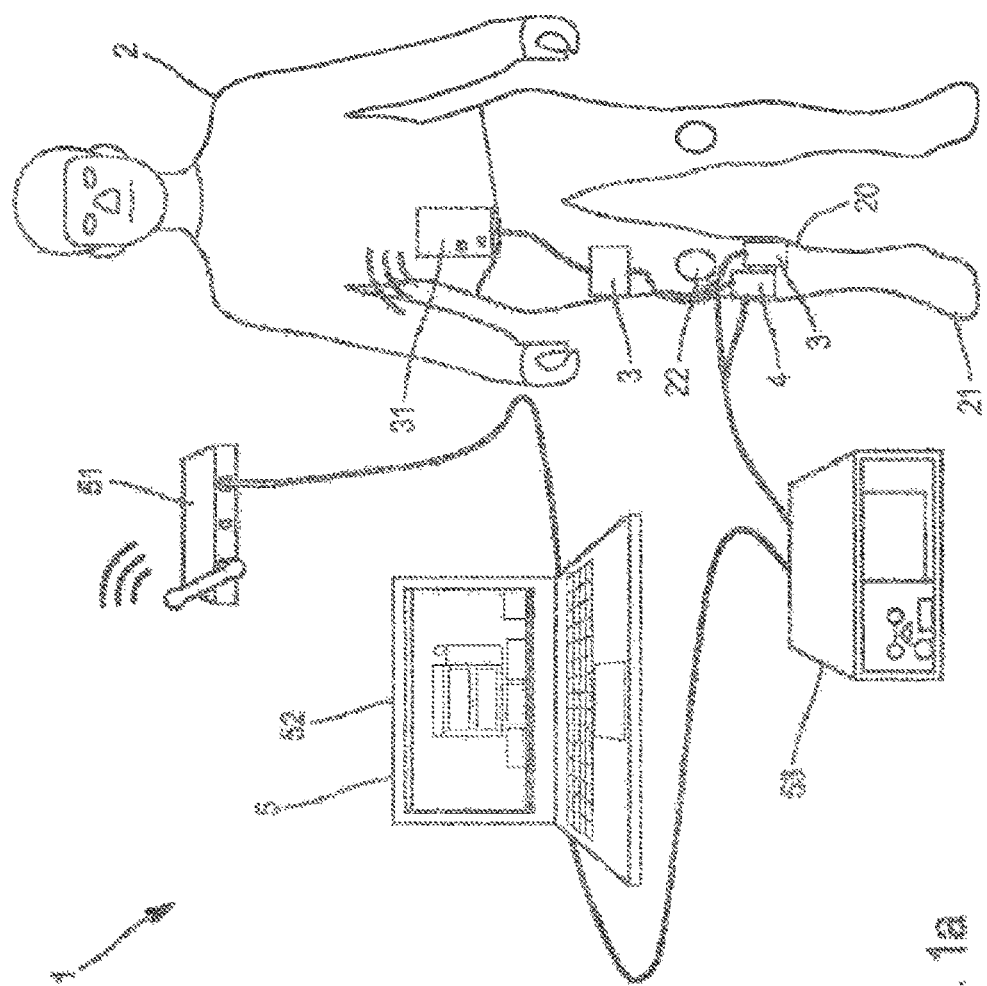

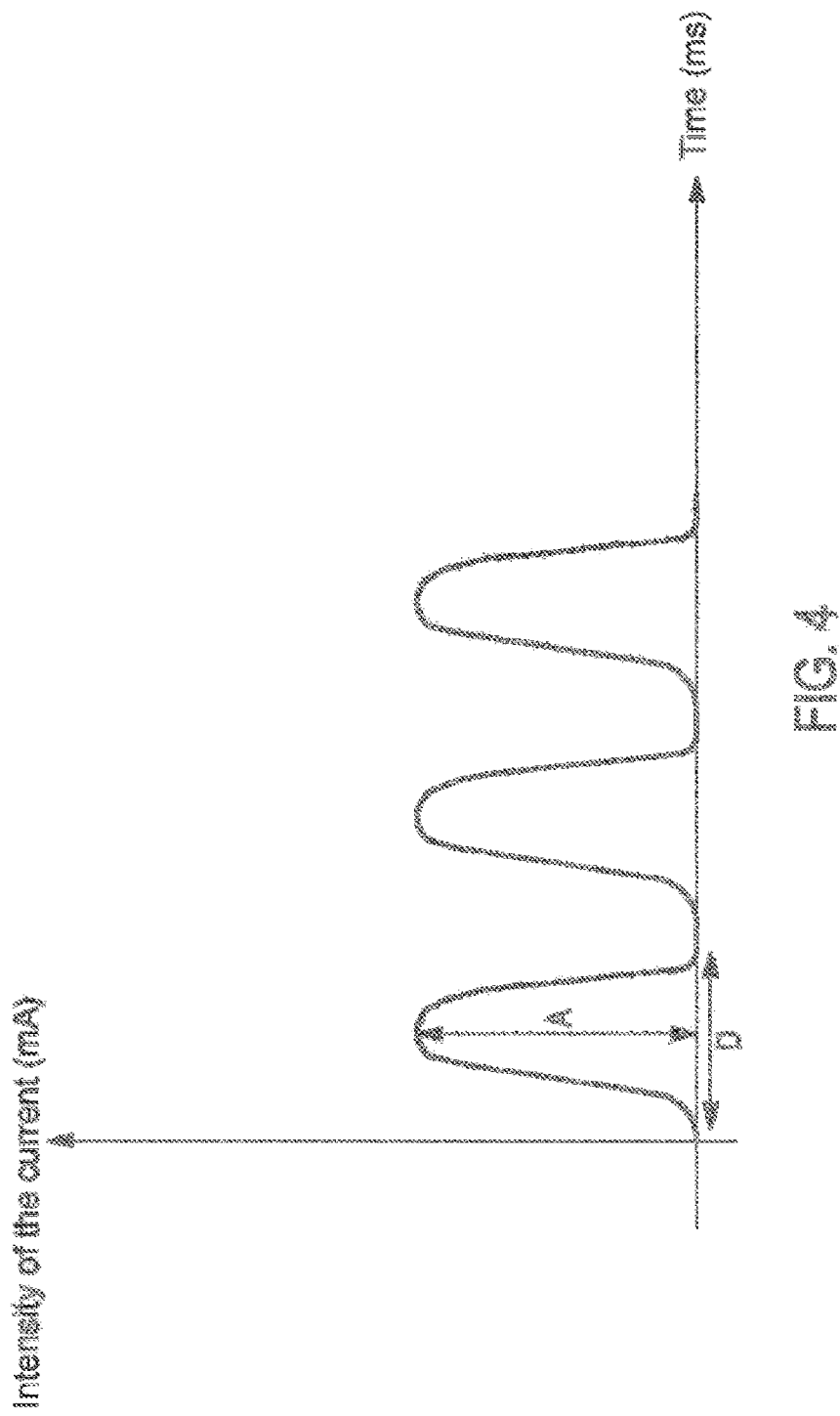

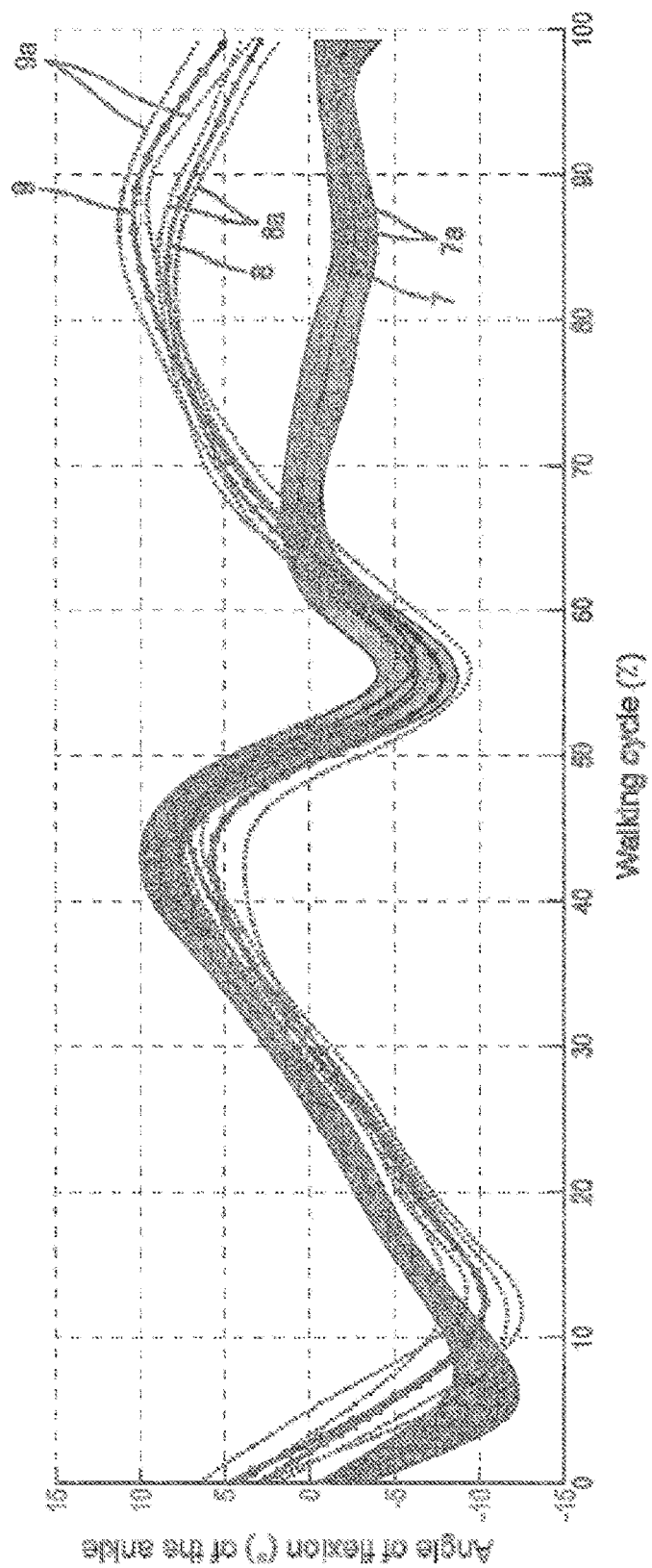

STIMULATION DEVICE FOR ACTIVATING AT LEAST ONE MUSCLE INVOLVED IN RAISING THE FOOT

CROSS-REFERENCE TO RELATED APPLICATIONS

The present application is a national phase entry under 35 U.S.C. § 371 of International Application No. PCT/EP2017/073235, filed Sep. 15, 2017, which claims priority from French Patent Application No. 1658930, filed Sep. 22, 2016, all of which are incorporated herein by reference.

FIELD OF THE INVENTION

The present invention relates to a device for stimulating at least one muscle involved in raising the foot of a user in order to activate said at least one muscle and thus facilitate walking of said user.

More particularly, the invention relates to a device of which stimulation of the muscle(s) involved in raising the foot is a function of the angle of flexion of the corresponding knee of the lower limb.

The invention also relates to a processing unit for such a stimulation device.

The invention also relates to a method for processing a signal for such a processing unit.

The invention also relates to a stimulation method for activating at least one muscle involved in raising the foot while an individual using the device according to the invention is walking.

The invention also relates to the use of the device according to the invention for individuals with spastic hemiparesis.

STATE OF THE ART

An individual with spastic hemiparesis, for example as a result of a cardiovascular event, may experience mobility problems due to a too rigid gait.

Indeed, the dorsiflexion movement of the ankle for raising the foot of the paralyzed lower limb of the hemiparetic individual may prove to be too limited, even absent.

A too limited, even absent, dorsiflexion movement, when the individual is walking, increases the risk for the foot to stumble into the ground and cause him to fall.

Such a deficiency in the dorsiflexion movement is due to a bad control of the muscles involved in raising the foot. These muscles are the following:
 the anterior tibial muscle (also called the tibialis anterior);
 the extender digitorum;
 the peroneal muscle, including the short peroneal.

In order to help the individual to raise the foot of the paralyzed lower limb, it is known to use an ankle and foot orthosis (AFO) that mechanically maintains said foot of said individual in the raised position.

However, such a solution tends to decrease the voluntary activation of the muscles responsible for the dorsiflexion, thus reducing the corticospinal excitability of the muscle activation control, thereby making the individual to depend on the orthosis.

There are also known devices for electrically stimulating the muscles of the individual which are responsible for the dorsiflexion, so as to activate said muscles when it is necessary that the individual raises the foot.

Thus, for example, document U.S. Pat. No. 4,796,631 is known, which describes a device for electrically stimulating the muscles involved in raising the foot while an individual is walking. The device described in this document comprises electrodes that are controlled to electrically stimulate the muscles during the stance phase, when both a sensor placed under the heel of the foot of the individual detects that the heel is on the ground, and that the angle of flexion of the knee of the same lower limb as the foot reaches a pre-established minimum value.

However, such a device, in addition to being bulky, requires that the individual wears shoes so that the heel sensor can be installed under the heel, and does not allow stimulating in a satisfactory manner the muscles responsible for the dorsiflexion.

Document "Modified implanted drop foot stimulator system with graphical user interface for customised stimulation pulse-width profiles" by T. O'Halloran, M. Haugland, G. M. Lyons, and T. Sinkjaer, is also known, which describes a device for electrically stimulating muscles involved in raising the foot while an individual is walking. The device described in this document comprises a processing unit that controls electrodes such that said electrodes electrically stimulate the muscles of the individual. The processing unit is configured so that the electrodes stimulate the muscles over 95% of the walking cycle of the individual both during the stance phase and the swing phase, the electrodes starting the electrical stimulation when the heel of the foot of the individual leaves the ground. In addition, the processing unit is configured so that the intensity of the stimulation increases when the heel of the foot touches the ground at the end of the swing phase. In order to notify the processing unit of the moment when the heel is in contact with the ground so that said processing unit can control the electrodes according to this information, the device comprises a pressure sensor disposed under the heel of the foot of the individual that detects when the heel is resting on the ground.

However, again, such a device is bulky because of the sensor that must be disposed under the heel of the individual and requires from the individual to wear shoes in order to place the sensor under the heel. The quasi-permanent stimulation is a factor of muscular fatigability and does not allow stimulating in a satisfactory manner the muscles responsible for the dorsiflexion.

Finally, there is also known a device for electrically stimulating the muscles involved in raising the foot of the paralyzed lower limb while the individual is walking, which comprises sensors measuring the inclination of the tibialis section of said lower limb in order to control the triggering of electrical stimulation according to the inclination of said tibialis section.

However, such a device does not allow stimulating in a satisfactory manner the muscles responsible for the dorsiflexion.

GENERAL PRESENTATION OF THE INVENTION

An object of the invention is to provide a stimulation technique for activating at least one muscle involved in raising the foot while an individual is walking, which allows solving the problems of the state of the art.

A first object of the invention is to trigger in an accurate manner the stimulation phase of the muscle(s), in order to ensure that the foot is raised at the appropriate time.

A second object of the invention is to ensure that raising the foot is sufficient at the end of the swing phase.

A third object of the invention is to reduce the electrical consumption of the stimulation while ensuring sufficient raising of the foot.

A fourth object of the invention is to reduce the bulk of the stimulation device, in particular by dispensing with the use of a pressure sensor disposed under the heel.

For this purpose, according to a first aspect of the invention, there is provided a stimulation device for activating at least one muscle involved in raising the foot while an individual is walking, comprising:

sensors configured to be placed on a lower limb of the individual and of which measurement signals allow calculating an angle of flexion of the knee corresponding to said lower limb;

electrodes configured to be placed on the muscle(s) to be activated and suitable for electrically stimulating said muscle(s);

a processing unit able to receive the measurement signal from the sensors, said processing unit having calculation means for calculating the value of the angle of flexion of the knee from the measurement signal received from the sensors, and comprising electrode control means connected to the calculation means and to the electrodes;

characterized in that the calculation means are configured to determine the swing phase in a walking cycle of the individual;

the control means are configured to:

activate the electrodes only during the swing phase of the walking cycle of the individual so that the electrodes generate electrical stimulation having an intensity as a function of the angle of flexion of the knee, activate the electrodes so that the electrodes generate electrical stimulation with an intensity that increases with the decrease of the angle of flexion of the knee, upon re-extension of the knee during the swing phase.

The device according to the invention is advantageously completed by the following characteristics, taken alone or in any of their technically possible combinations:

the processing unit is configured to determine, in the swing phase, an initial-swing sub-phase and a terminal-swing sub-phase, and to activate the electrodes so that the electrodes generate electrical stimulation with an intensity that increases between a first threshold value and a second threshold value of the angle of flexion of the knee, the first threshold value being reached in the initial-swing sub-phase, and the second threshold value being reached in the terminal-swing sub-phase;

the processing unit is configured to activate the electrodes such that the electrodes generate electrical stimulation with an intensity that increases between a first threshold value and a second threshold value, the first threshold value being the angle of flexion of the knee of the individual at the beginning of the re-extension of the knee, and the second threshold value being the angle of flexion of the knee of the individual at the end of the re-extension of the knee occurring in a terminal-swing sub-phase of the swing phase;

the processing unit is configured to activate the electrodes such that the electrodes generate electrical stimulation having an intensity pulse between an initial-swing sub-phase and the beginning of the extension of the knee;

the processing unit is configured to control the electrodes such that said electrodes generate electrical pulses during the swing phase, the electrical pulses being defined by an amplitude corresponding to the intensity of the current applied to the electrodes, the increase in the intensity of the stimulation during the stimulation phase by said electrodes being carried out by increasing the amplitude;

the processing unit is configured to control the electrodes so that the intensity of the stimulation increases linearly with the decrease of the angle of flexion upon re-extension of the knee;

the processing unit is configured to control the electrodes so that the intensity of the stimulation increases linearly with the increase of the angle of flexion during the increase of the angle of flexion of the knee during the swing phase;

the processing unit determines the angle of flexion of the knee without being connected to a plantar pressure sensitive sensor;

the sensors comprise a first inertial measurement unit and a second inertial measurement unit;

the device further comprises a first fastener for attaching the first inertial measurement unit to a thigh of the lower limb, and a second fastener for attaching the second inertial measurement unit to a tibialis section of said lower limb.

According to a second aspect, the invention also relates to a processing unit for activating at least one muscle involved in raising the foot while an individual is walking, configured to receive measurement signals from sensors and having:

calculation means for determining the value of the angle of flexion of the knee of the lower limb of the individual from said at least one received measurement signal, and for determining the swing phase in a walking cycle of the individual;

control means connected to the calculation means for controlling electrodes as a function of the value of the determined angle of flexion of the knee;

in that the control means generate a control signal triggering a stimulation phase by said electrodes only during the swing phase of the walking cycle of the individual:

so that the electrodes generate electrical stimulation the intensity of which is a function of the angle of flexion of the knee and which increases with the decrease of the angle of flexion of the knee, upon re-extension of the knee during the swing phase.

According to a third aspect, the invention also relates to a processing method for a processing unit according to the second aspect, comprising the following steps:

receiving a measurement signal from sensors allowing to measure an angle of flexion of the knee of a lower limb of an individual;

determining the value of the angle of flexion of the knee from the measurement signal received in the previous step and determining the swing phase in a walking cycle of the individual;

generating a control signal only during the swing phase detected in the previous step, so that:

the electrodes generate electrical stimulation which increases with the decrease of the angle of flexion of the knee upon re-extension of the knee during the swing phase.

According to a fourth aspect, the invention also relates to a computer program product comprising program code instructions for performing the steps of the signal processing method according to the third aspect.

According to a fifth aspect, the invention also relates to a medium that can be used in a computer on which the computer program product is recorded according to the fourth aspect.

According to a sixth aspect, the invention relates to a stimulation method for activating at least one muscle involved in raising the foot while an individual is walking, comprising the following steps:

measuring an angle of flexion of a knee of the individual and detecting the swing phase of the walking cycle of the individual from the measured value of the angle of flexion of the knee;

triggering an electrical stimulation phase of the muscle(s) only during the swing phase of a walking cycle of the individual, the electrical stimulation being a function of the angle of flexion of the knee, and increasing with the decrease of the angle of flexion of the knee upon re-extension of the knee during the swing phase.

According to an additional characteristic of the stimulation method, the stimulation is periodically triggered for n walking cycles of the individual among N considered walking cycles, n being a natural number greater than or equal to 2 and strictly less than N, N being a number of walking cycle.

For example, the control means can send a stimulation one walking cycle out of two, so that the user can try himself to raise the foot, before being again assisted by the stimulation controlled by the control means to the electrodes, and so on.

According to a seventh aspect, the invention relates to a use of the device according to the first aspect of the invention for neurological patients with spastic paresis.

PRESENTATION OF THE FIGURES

Other characteristics, objects and advantages of the invention will appear upon reading the following description of various embodiments shown in the following drawings:

FIG. 1a schematically shows a stimulation device on an individual;

FIG. 1b schematically shows a stimulation device on a lower limb of an individual;

Figure 5A:
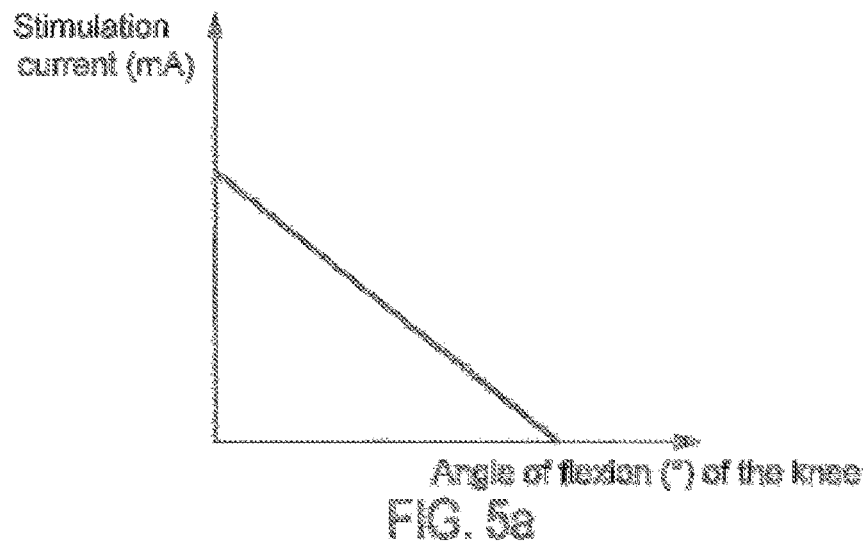
Figure 5B:
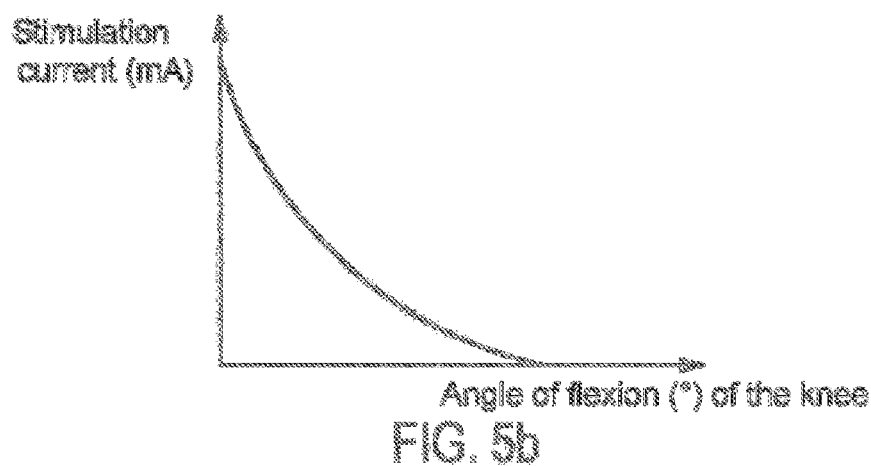
Figure 5C:
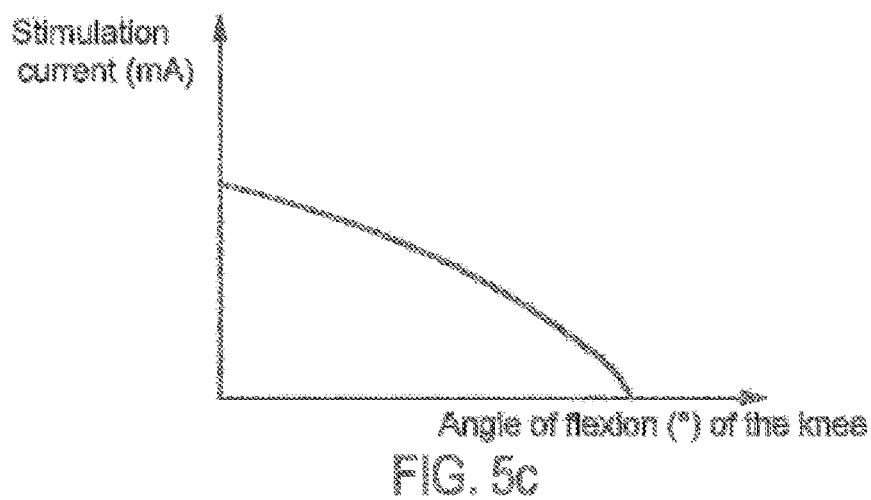
Figure 7:
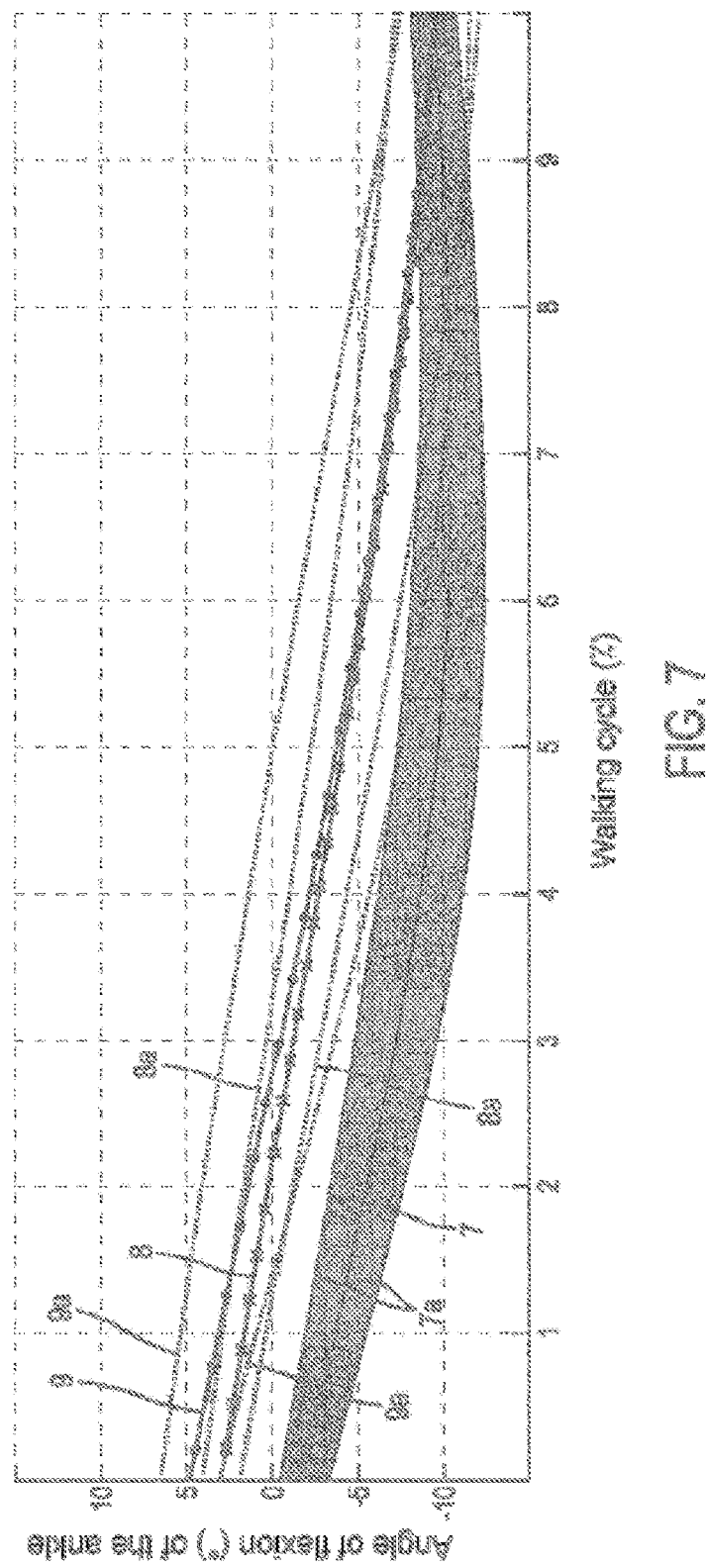
Figure 8:
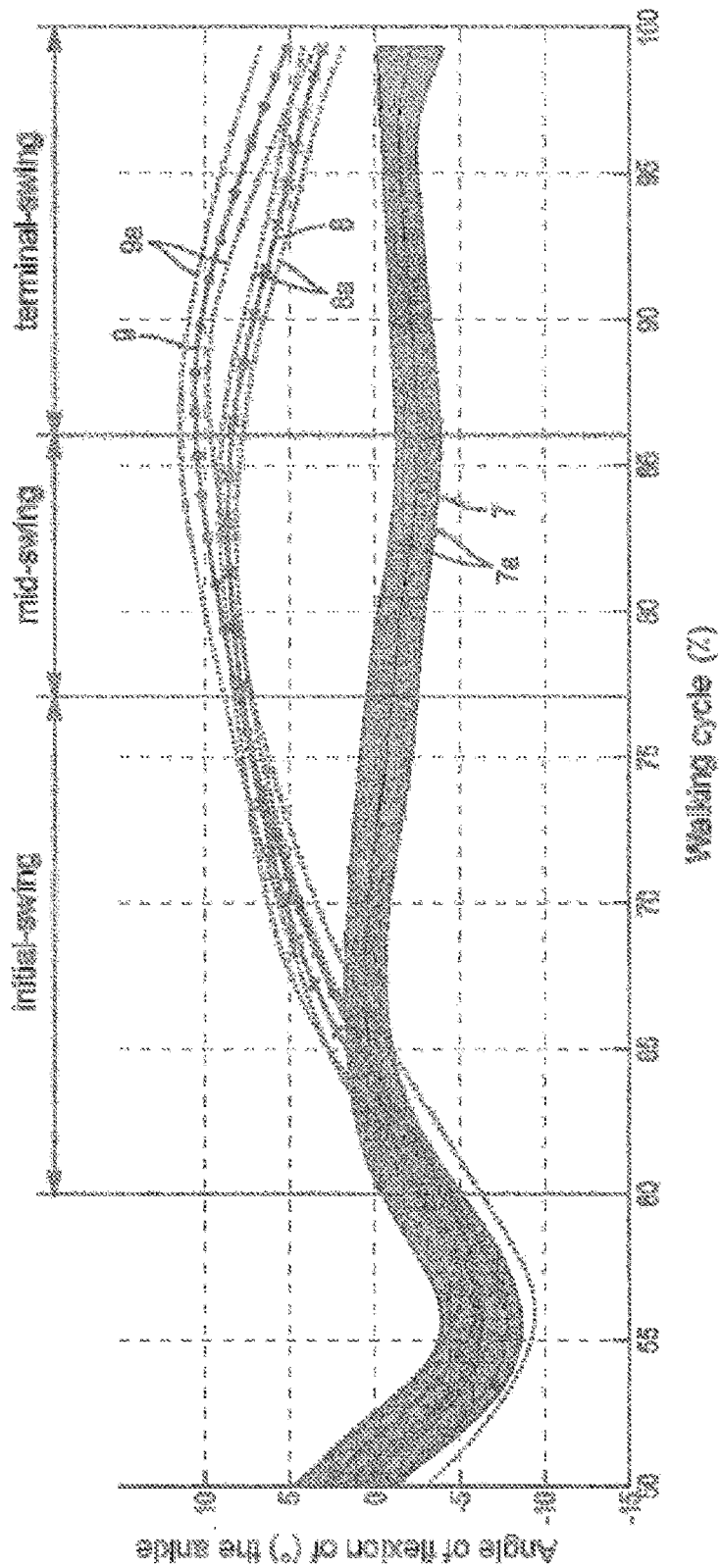
Figure 9:
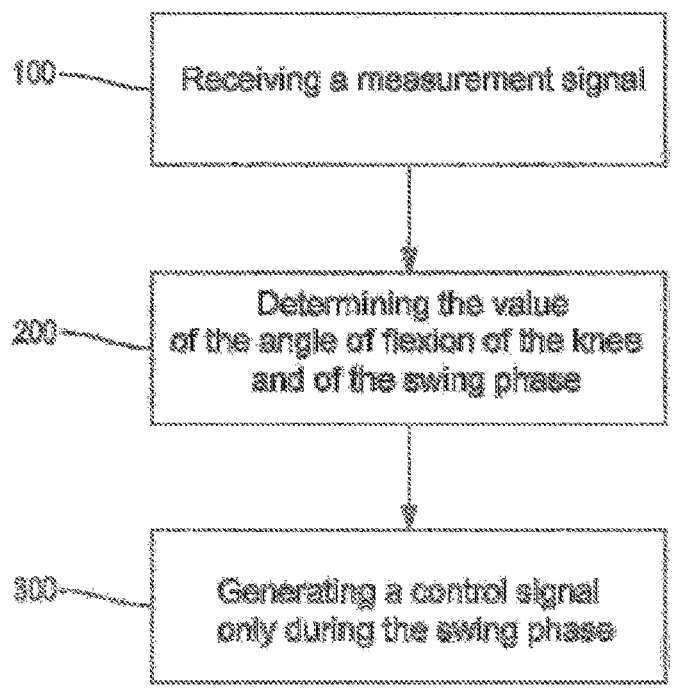
Figure 10:
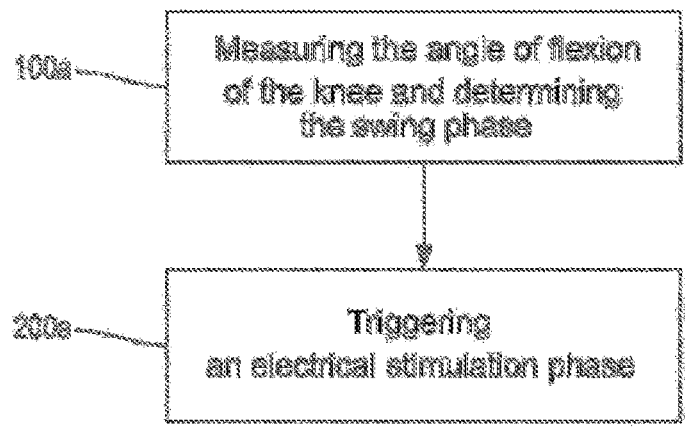

FIG. 4 schematically shows electrical pulses created by electrodes to stimulate one or more muscle(s);

FIG. 5a shows a variant of possible function between the angle of flexion of the knee and the intensity of the stimulation current;

FIG. 5b shows an additional variant of possible function between the angle of flexion of the knee and the intensity of the stimulation current;

FIG. 5c shows yet another variant of possible function between the angle of flexion of the knee and the intensity of the stimulation current;

FIG. 6 shows, on a complete walking cycle, the comparison of the variation of the angle of flexion of the ankle between unstimulated individuals, stimulated individuals whose stimulation intensity is constant during the stimulation phase, and stimulated individuals according to the invention;

FIG. 7 shows a more precise view of FIG. 6 between 0% and 10% of the walking cycle;

FIG. 8 shows a more precise view of FIG. 6 between 50% and 100% of the walking cycle;

FIG. 9 shows a possible implementation of a signal processing method for a processing unit according to the invention;

FIG. 10 shows a possible implementation of a stimulation method for activating at least one muscle involved in raising the foot while an individual is walking according to the invention.

DESCRIPTION OF THE INVENTION

Figure 1B:
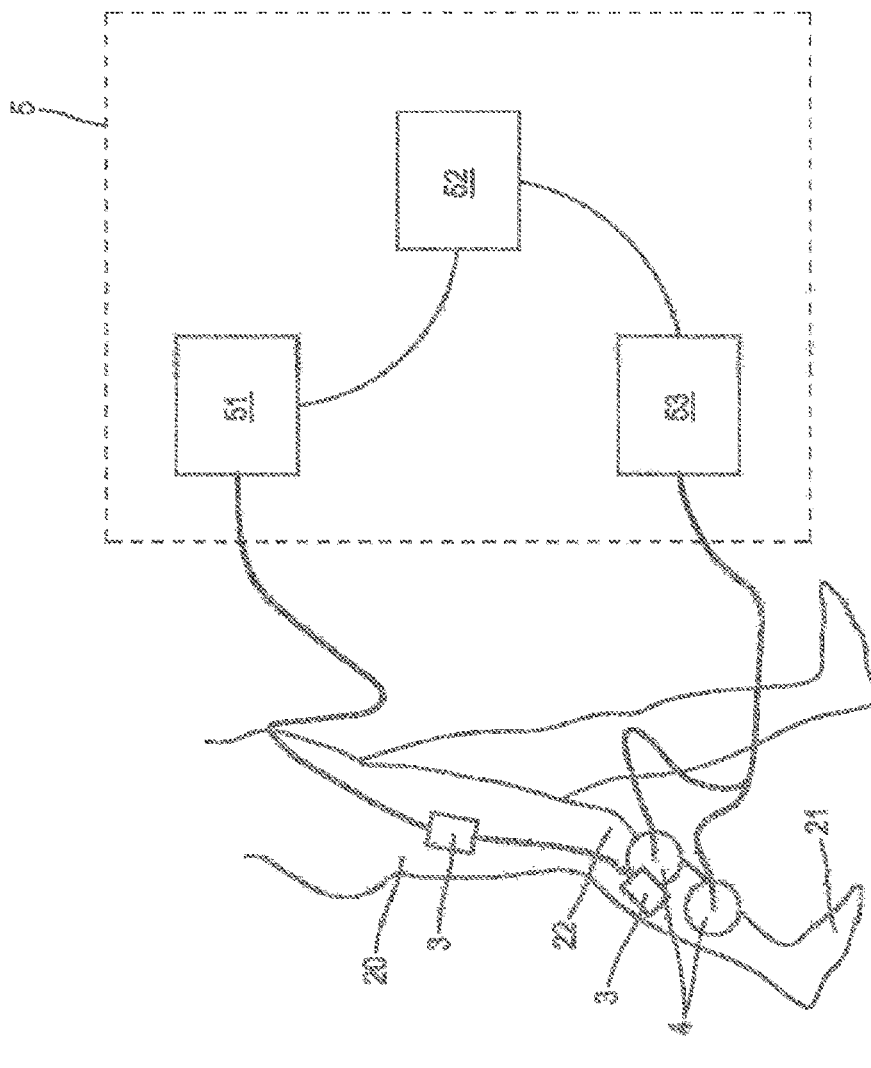

As illustrated in FIG. 1a and FIG. 1b, the stimulation device 1 for activating at least one muscle involved in raising the foot 21 of a lower limb 20 of an individual 2 while said individual 2 is walking, comprises the following elements:

sensors 3 on the deficient lower limb 20 of the individual 2 which measure the angle of flexion of the knee 22 of said lower limb 20;

at least two electrodes 4 on the lower limb 20 facing the muscle(s) to be activated in order to electrically stimulate said muscle(s);

a processing unit 5 which controls the electrodes 4 as a function of the value of the angle of flexion of the knee 22 measured by the sensors 3.

According to a possible variant, the sensors 3 may be inertial measurement units (also called IMU). In this variant, a first inertial measurement unit is placed on the thigh of the individual 2, and a second inertial measurement unit is placed on the tibialis section of the individual 2. The inertial measurement units comprise, according to a possible variant, three gyrometers and three accelerometers. The three gyrometers of each inertial measurement unit allow measuring the three components of the angular speed of the thigh of the tibialis section, and the three accelerometers of each inertial measurement unit allow measuring the three components of the linear acceleration of said thigh and said tibialis section.

The angle of flexion of the knee 22 measured by the sensors 3 is the angle formed by the inclination of the tibialis section relative to the thigh. Thus, when the lower limb 20 of the individual 2 is stretched, i.e. the tibialis section and the thigh are aligned, then the angle of flexion of the knee 22 is equal to 0°.

The sensors 3 transmit, via a transmitter 31, a measurement signal which is transmitted to the processing unit 5. The processing unit 5 comprises a receiver 51 which picks up the measurement signal transmitted by the transmitter 31 of the sensors 3, the processing unit 5 being connected to the sensors 3, through said receiver 51. The measurement signal can be transmitted from the sensors 3 to the processing unit 5 in a wired or wireless manner, for example by Wi-Fi.

The processing unit 5 comprises calculation means 52 comprising a processor as well as a memory. The calculation means 52 process the measurement signal sent by the sensors 3 and calculate the value of the angle of flexion of the knee 22 from said measurement signal. The sensors 3 and the processing unit 5 allow measuring in real time the angle of flexion of the knee 22.

In addition, the calculation means 52 detect the different phases of the walking cycle of the individual from the variation of the value of the angle of flexion of the knee 22 over time or from other parameters known from the state of the art.

Figure 2:
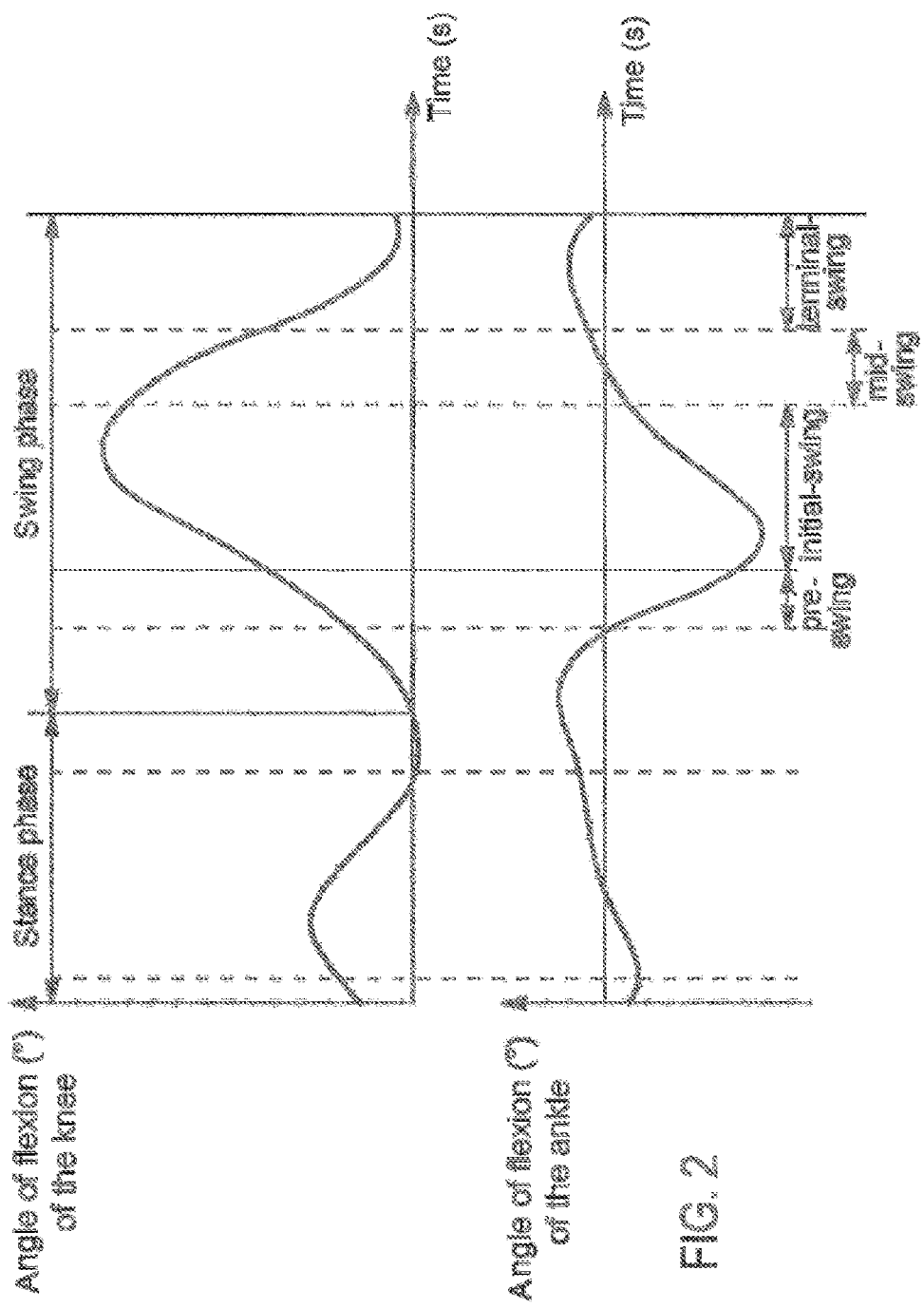
FIG. 2 shows, in the form of curves, the evolution of the angle of flexion of the knee and the angle of flexion of the ankle during the walking cycle of an individual.

Indeed, as shown in FIG. 2, the walking cycle of an individual is divided into two major phases: the stance phase during which the foot 21 stays on the ground and the individual raises the other foot and moves it forward, and the swing phase during which the individual raises the foot 21 to bring it ahead and sets said foot 21 on the ground. The stance phase ends and the swing phase begins when the heel of the foot 21 leaves the ground.

During the stance phase, as seen in FIG. 2, the individual has a flexion movement of the knee 22 of small amplitude, which is followed by an extension movement of the knee 22 of small amplitude too. During the swing phase, the individual 2 has a flexion movement of the knee 22 of high amplitude which is followed by an extension movement of the knee 22 of high amplitude too. The extension movement of the knee 22 of high amplitude during the swing phase is called "re-extension of the knee 22" according to the terminology of the technical field. This re-extension of the knee 22 corresponds to the movement that the individual 2 makes when his foot 21 is in the air and when he extends the lower limb 20 until setting the heel of the foot 21 on the ground. The re-extension begins for example from 50° in FIG. 3b from which the angle of flexion decreases, in the "mid-swing" phase.

As illustrated in FIG. 2, the calculation means 52 of the processing unit 5 detect the stance phase and the swing phase by detecting, for each cycle, two peaks of different values in the variation of the value of the angle of flexion of the knee 22 over time, a first low-value peak corresponding to the stance phase, and a second high-value peak corresponding to the swing phase.

Moreover, the calculation means 52 of the processing unit 5 detect the different sub-phases that constitute the stance and swing phases of the walking cycle of the individual 2. Thus, the calculation means 52 detect:

a pre-swing sub-phase which starts the swing phase by making the transition with the end of the stance phase. The pre-swing sub-phase begins when the heel of the foot 21 leaves the ground, and ends when the toes of the foot 21 leave the ground;

an initial swing sub-phase which follows the pre-swing sub-phase and in which the value of the angle of flexion reaches its maximum corresponding to the previously detected high-value peak. The initial swing sub-phase begins when the toes of the foot 21 leave the ground, and ends when the foot 21 of the individual 2 is at the same level as the other foot of said individual 2;

a mid-swing sub-phase which follows the initial swing sub-phase and which corresponds to the beginning of the re-extension of the knee 22. The mid-swing sub-phase begins when both feet of the individual 2 are at the same level, and ends when the tibialis section of the lower limb 20 is vertical (perpendicular relative to the ground);

a terminal-swing sub-phase which follows the mid-swing sub-phase and which corresponds to the end of the re-extension of the knee 22, said terminal-swing sub-phase ending when the heel of the foot 21 of the individual 2 sets on the ground. A new stance phase of a new walking cycle begins following the terminal-swing sub-phase.

The processing unit 5 comprises control means 53 of the electrodes 4. The control means 53 generate a control signal which activates the electrodes 4 so that said electrodes 4 trigger a stimulation phase of the muscle(s) only during the swing phase of the walking cycle of the deficient lower limb 20 of the individual 2.

In order for the control means 53 to activate the electrodes 4 only during the swing phase of the walking cycles of the individual 2, said control means 23 generate the control signal only when the value of the angle of flexion of the knee 22 reaches a first threshold value. This first threshold value can be adapted so that it corresponds to a position of the knee 22 when the individual is in the initial swing sub-phase.

Figure 3A:
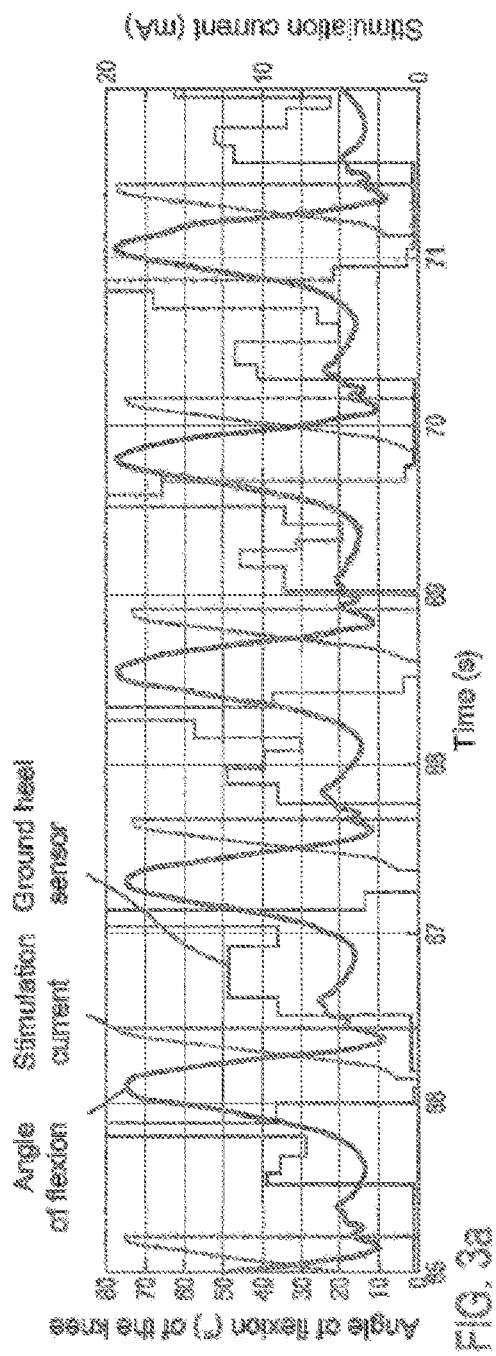
FIG. 3a shows the evolution of the angle of flexion of the knee, the evolution of the intensity of the stimulation current created by electrodes, and the response of a pressure sensor located under the heel for a healthy individual.
Figure 3B:
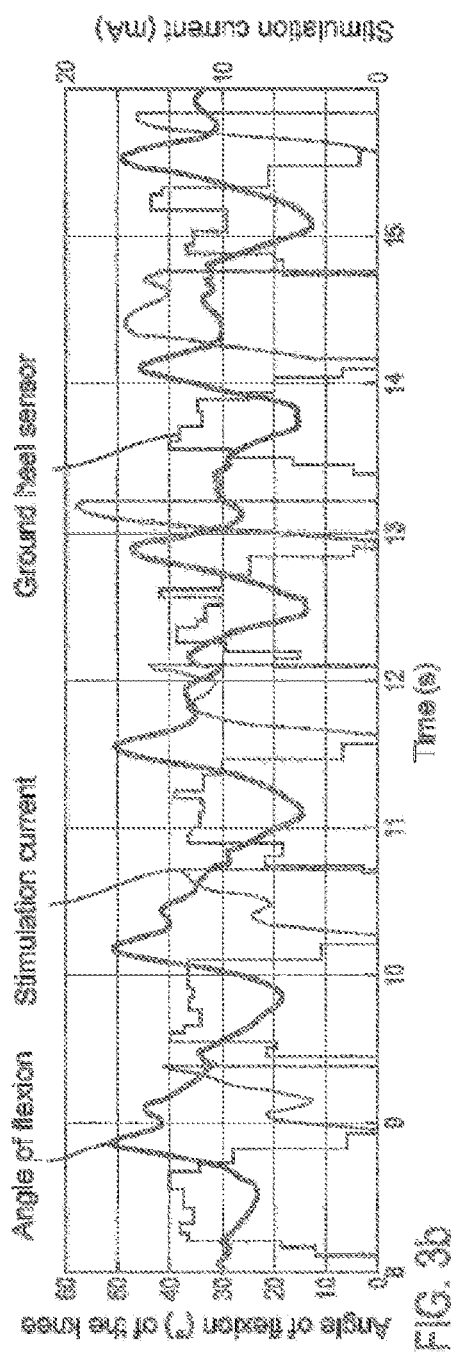
FIG. 3b shows the evolution of the angle of flexion of the knee, the evolution of the intensity of the stimulation current created by electrodes, and the response of a pressure sensor located under the heel for an individual with spastic hemiparesis.

The value of the first threshold is set by the physiotherapist at the moment of installation of the device 1 on the individual 2. As seen in FIGS. 2, 3a and 3b, the value of the first threshold must be, on the one hand, sufficiently high so that the stimulation phase is not triggered during the stance phase and, on the other hand, sufficiently low so that the stimulation phase is triggered during the swing phase. In other words, it is necessary that the first threshold is, on the one hand, greater than the value of the first peak (the peak of the stance phase) that the value of the angle of flexion of the knee 22 reaches and, on the other hand, less than or equal to the second peak (the peak of the swing phase) that the value of the angle of flexion of the knee 22 reaches.

The value of the first threshold may be equal to the value of the angle of flexion of the knee 22 at the beginning of the re-extension of the knee 22 during the swing phase, i.e. to the value of the second peak corresponding to the swing phase.

In addition, so that the control means 53 activate the electrodes 4 only during the swing phase, said control means 23 stop generating the control signal activating the electrodes 4 when the value of the angle of flexion of the knee 22 is less than a second threshold value which is less than the first threshold value. This second threshold value can be chosen so that it corresponds to a position of the knee 22 when the individual is in the terminal-swing sub-phase.

The value of the second threshold may be equal to the value of the angle of flexion of the knee 22 at the end of the re-extension of the knee 22.

As seen in FIG. 3b, the individual 2 being hemiparetic, the knee 22 does not flex in a normal manner during the walking cycle of said individual 2. Thus, the individual 2 can have a very stiff lower limb 20 and flex only very slightly the knee 22 while walking, so that the angle of flexion of the knee 22 always remains very close to 0° throughout the walking cycle. In another possible case, the individual can keep the knee 22 permanently flexed, so that the angle of flexion of the knee 22 shall never be equal to 0°. This is why it is necessary for the physiotherapist to adapt the value of the first threshold and of the second threshold according to the individual. Moreover, as seen in FIGS. 3a and 3b, the stance phase of the walking cycle and the swing phase of the individual 2 may be deformed compared to the phases of the walking cycle of a healthy individual.

According to a possible variant, instead of stopping the activation of the electrodes 4 below the second threshold value, the activation of the electrodes 4 is stopped when the calculation means 52 of the processing unit 5 detect a minimum in the variation of the value of the angle of flexion of the knee 22. The minimum is detected when the value of the angle of flexion of the knee 22 increases after having decreased during the re-extension of said knee 22.

According to an additional variant, the stopping of the stimulation phase during which the electrodes 4 are activated is carried out when, on the one hand, the value of the angle of flexion crosses the second threshold and, on the other hand, when the minimum is detected. Such a variant makes it possible, on the one hand, to take into account the variability of the minimum value reached by the angle of flexion of the knee 22 during different walking cycles that follow each other and, on the other hand, makes it possible not to take into account the minimums in the variation of the angle of flexion of the knee 22 during the swing phase that are caused by spasms of the lower limb 20 of the individual 2 and that occur before the end of the re-extension of the knee 22.

According to a preferred variant, the stimulation phase of the muscle(s) by the electrodes 4 is performed only upon re-extension of the knee 22 during the swing phase, the intensity of the stimulation increasing gradually during the re-extension of said knee 22.

However, according to another possible variant, the processing unit 5 triggers the stimulation phase before the re-extension of the knee 22, for example during the pre-swing sub-phase during which the knee 22 flexes. In this variant, it is possible for the stimulation phase to start with a peak of stimulation intensity, the stimulation intensity decreasing gradually until re-extension of the knee 22 (i.e. until the value of the angle of flexion of the knee 22 reaches the first threshold) and starting from said re-extension of the knee 22, the intensity gradually increases until the end of the swing phase.

The stimulation phase by the electrodes 4 is triggered by passing an electric current through the electrodes 4 thereby forcing the muscle(s) traversed by said electric current to contract. The electrodes 4, at least two, are therefore arranged opposite the muscle(s) to be stimulated. Said electrodes 4 are placed by the physiotherapist when positioning the device 1 on the individual 2 in order to adapt the placement of the electrodes 4 according to the morphology of the individual 4. The electrodes 4 are therefore arranged opposite the anterior tibia muscle, and/or the extender digitorum, and/or the peroneal muscles. In addition, for a given position of the electrodes 4, the modification of the intensity of the electric current sent by the electrodes also makes it possible to modify the stimulated muscles because a weak intensity stimulates only the muscle(s) located in the vicinity of the skin (and therefore of the electrodes 4), while a high intensity allows stimulating one or several muscle(s) that are located deeper in the lower limb (and that are therefore relatively away from the electrodes 4).

The intensity of the current sent by the electrodes 4 is set by the physiotherapist in order to adapt the intensity of the current sent by the electrodes 4 according to the morphology of the individual, his level of paralysis, and his endurance. For example, for a very corpulent person, it is necessary that the intensity of the current sent by the electrodes 4 is greater than for a less corpulent person in order to stimulate in the same way the desired muscle(s). The intensity of the current of the electrical pulses is preferably comprised between 20 mA and 40 mA.

In order to pass an electric current through the electrodes 4, the device 1 comprises a battery connected to said electrodes 4 which stores electrical energy in order to electrically supply the electrodes 4 only during the stimulation phase.

The intensity of the stimulation carried out by the electrodes 4 during the stimulation phase is a function of the angle of flexion of the knee 22. This ensures a high stimulation intensity at the end of the swing phase, and more precisely at the end of the re-extension of the knee 22, relative to the rest of the stimulation phase.

Increasing accordingly the intensity of the stimulation during the stimulation phase allows the foot 21 to be further raised at the end of the stimulation phase. Indeed, the applicant has observed that it is preferable that the foot is further raised at the end of the swing phase (terminal-swing sub-phase), which corresponds to the end of the re-extension of the knee 22.

Indeed, in the stimulations carried out in the prior art, the intensity of the stimulation does not vary during the stimulation phase, so that the curve of the stimulation intensity over time forms a slot in which the intensity is at 0 outside the stimulation phase, and the intensity is at 1 during the stimulation phase.

These solutions of the state of the art require strongly stimulating the muscles from the very beginning of the stimulation phase which, on the one hand, consumes more energy and, on the other hand, tires the individual 2 easily.

The invention thus makes it possible to limit the electrical consumption of the device 1, thereby making it possible to gain autonomy and to reduce the bulk of the battery supplying the electrodes 4 with electricity. In addition, the invention makes it possible to reduce the fatigue of the individual 1 by stimulating the muscle(s) of the lower limb 20 only where useful, and with an intensity adapted according to the movement of the lower limb 20 that said individual 1 is undertaking.

In addition, increasing the intensity of the stimulation during the re-extension of the knee 22 makes it possible to counteract the contraction reflex of the muscles opposed to the dorsiflexion movement, thereby ensuring that the foot 21 is sufficiently raised when the individual 2 sets said foot 21 on the ground.

As illustrated in FIG. 4, the electrical stimulation of the electrodes 4 is preferably performed by applying a succession of electrical pulses on the muscle(s) with the electrodes 4. The electrical pulses transmitted by the electrodes 4 are defined by the following parameters:

An amplitude A, which corresponds to the intensity of the current sent during the pulse. A is preferably comprised between 20 mA and 40 mA.

A frequency, which corresponds to the number of pulses transmitted in unit time. The frequency is preferably comprised between 10 Hz and 30 Hz, and is even more preferably equal to 20 Hz. With a frequency of 20 Hz, the muscles affected by electrical pulses do not have time to relax.

a duration D, which corresponds to the time during which each pulse is applied. D is preferably comprised between 2 and 10 µs, and is even more preferably equal to 5 µs.

The intensity of the electrical stimulation can be increased (or decreased) by increasing (or decreasing) the amplitude A of the pulses, and/or the frequency of said pulses, and/or the duration D of said pulses.

The stimulation intensity curves shown in FIGS. 3a and 3b are formed by connecting the peaks of the electrical pulses generated by the electrodes 4.

The intensity of the stimulation by the electrodes 4 during the stimulation phase is a function of the angle of flexion of the knee 22, the intensity of the stimulation increasing when the angle of flexion of the knee 22 decreases during the re-extension of the knee 22.

In the example given in FIG. 5a, the intensity of the stimulation is inversely proportional to the angle of flexion of the knee 22, the intensity therefore increasing linearly relative to the angle of flexion.

In the example given in FIG. 5b, the intensity of the stimulation increases hyperbolically when the angle of flexion of the knee 22 decreases.

In the example given in FIG. 5c, the intensity of the stimulation increases logarithmically when the angle of flexion of the knee 22.

Other functions are also possible, the intensity of the stimulation being able to increase exponentially or parabolically when the angle of flexion of the knee 22 decreases.

In the examples given in FIGS. 5a, 5b and 5c, the increase of the stimulation intensity is achieved by increasing the intensity of the electric current transmitted by the electrodes 4 during the stimulation phase, for example by increasing the amplitude A of the electrical pulses transmitted by the electrodes). However, the increase in the intensity of the stimulation can also be obtained by increasing the frequency of the electrical pulses, and/or the duration D of said electrical pulses.

According to one possible variant, the stimulation intensity controlled by the processing unit 5 at the electrodes 4 increases when the angle of flexion of the knee 22 increases during the pre-swing sub-phase and the initial swing sub-phase.

As seen in FIGS. 3a and 3b, which represent different stimulation phases by using a possible variant of the device 1 according to the invention, on the one hand, on a healthy individual (FIG. 3a) and, on the other hand, on a hemiparetic individual (FIG. 3b), the stimulation phase is performed during the re-extension of the knee 22. The intensity of the stimulation (here the intensity of the current generated by the electrodes 4) is maximum just at the end of the re-extension movement of the knee 22 before the heel touches the ground. The heel touches the ground when the curve representing the ground heel sensor is greater than 0. The ground heel sensor is here used only to make visible in FIGS. 3a and 3b the moment when the individuals set their heel on the ground, the device 1 according to the invention however does not need such a ground heel sensor to operate. Indeed, the device 1 can detect the different phases of the walking cycle of the individuals only from the sensors 3.

FIG. 6 represents the angle of flexion of the ankle of individuals 2 throughout a walking cycle, so as to compare the use of the device 1 according to the variant of FIGS. 1a and 1b, on the one hand, with a device that generates a stimulation phase during which the stimulation intensity does not vary and, on the other hand, with an unstimulated individual. The variant of the device 1 used here varies the stimulation intensity by varying the intensity of the electric current sent by the electrodes 4 during the stimulation phase.

The curve 7 represents the mean of the ankle flexion angle for unstimulated individuals, and the curves 7a represent the standard deviation of the ankle flexion angle for unstimulated individuals.

The curve 8 represents the mean of the ankle flexion angle for individuals who were stimulated with constant stimulation intensity during the stimulation phase, and the curves 8a represent the standard deviation of the ankle flexion angle for individuals who have been stimulated with constant stimulation intensity during the stimulation phase.

The curve 9 represents the mean of the ankle flexion angle for individuals who were stimulated with the device according to the invention, i.e. with a stimulation intensity which increases during the stimulation phase and the maximum of which occurs in the terminal-swing sub-phase and corresponds to the stimulation intensity used for the constant-intensity stimulation of the curve 8. The curves 9a represent the standard deviation of the ankle flexion angle for individuals who have been stimulated with the device according to the invention.

As seen in FIG. 6, the electrical stimulation makes it possible to substantially increase the amplitude of the dorsiflexion movement during the swing phase. In addition, the device according to the invention allows the individuals 2 to further raise the foot 21, the amplitude of the dorsiflexion movement being greater than the end of the swing phase. The fact that the amplitude of the dorsiflexion movement with the device according to the invention is greater is all the more remarkable as the electrical power sent by the electrodes is less than the electrical power sent by the electrodes of the device in which the stimulation intensity does not vary.

As illustrated in FIG. 7, which details the beginning of the stance phase, the device 1 according to the invention makes it possible to have a greater dorsiflexion of the ankle at the beginning of the stance phase compared to the device for which the stimulation intensity does not vary. The mean of the difference in the ankle flexion angle on this part of the walking cycle (from 0% to 10% of the walking cycle), between the case where the individual is not stimulated and the case where the individual is stimulated with the device according to the invention, is of 5.134°. The mean of the difference in the ankle flexion angle on this part of the walking cycle, between the case where the individual is not stimulated and the case where the individual is stimulated without varying the intensity of the stimulation is of 4.451°.

As illustrated in FIG. 8, which details the swing phase, the device 1 according to the invention makes it possible to have a greater dorsiflexion movement of the ankle only during the mid-swing sub-phase (from 77% to 86% of the cycle) and the terminal-swing sub-phase (from 86% to 100% of the cycle). Indeed, on the initial-swing sub-phase (from 60% to 77% of the cycle), the dorsiflexion movement is greater with the device in which the stimulation intensity is constant. However, this difference in the amplitude of the dorsiflexion movement is small. The mean of the difference in the angle of flexion during the initial-swing sub-phase (from 60% to 77%) between the case where the individual is not stimulated and the case where the individual is stimulated without varying the stimulation intensity is of 3.184°. The mean of the difference in the angle of flexion during the initial-swing sub-phase (from 60% to 77% of the cycle) between the case where the individual is not stimulated and the case where the individual is stimulated by varying the stimulation intensity is of 2.642°.

For the mid-swing sub-phase (from 77% to 86% of the cycle), the mean of the difference in the angle of flexion between the case where the individual is not stimulated and the case where the individual is stimulated by varying the stimulation intensity is of 10.744°, while the mean of the difference in the angle of flexion between the case where the individual is not stimulated and the case where the individual is stimulated with a constant stimulation intensity is of 9.917°.

For the terminal-swing sub-phase (from 86% to 100% of the cycle), the mean of the difference in the angle of flexion between the case where the individual is not stimulated and the case where the individual is stimulated by varying the stimulation intensity is of 10,721°, while the mean of the difference in the angle of flexion between the case where the individual is not stimulated and the case where the individual is stimulated with a constant stimulation intensity is of 8.047°.

Moreover, as illustrated in Table 1, which compares the mean time taken by an individual equipped with a stimulation device of the dorsiflexor muscles to travel a 10 meter distance while walking, the mean speed of travel of the individual, and the mean length of his strides, when said individual is not stimulated, when the intensity of the stimulation is constant, and when the stimulation intensity increases according to the invention.

TABLE 1

|  | Mean duration (s) | Mean speed (m/s) | Mean length of the strides (m) |
|---|---|---|---|
| Without stimulation | 9.558 | 1.049 | 0.619 |
| Constant stimulation | 9.650 | 1.037 | 0.677 |
| Device according to the variant of FIGS. 1a et 1b | 9.430 | 1.068 | 0.660 |

As shown in Table 1, the invention allows the individual to move faster, even if his strides are slightly shorter than when the stimulation intensity is constant.

In order to allow the sensors 3 to be attached on the lower limb 20 of the individual 2, the device 1 comprises fasteners. A first fastener allows attaching a sensor 3 on the thigh of the lower limb 20 of the individual 2, and a second fastener allows attaching another sensor 3 on the tibialis section of said lower limb 20. Thus, when the sensors 3 comprise two inertial measurement units, a first inertial measurement unit is attached on the thigh by the first fastener, and a second inertial measurement unit is attached on the tibialis section by the second fastener.

The fasteners may be formed of a band wound around the desired part of the lower limb 20 of the individual 2.

As represented in FIG. 9, the method for processing a signal for the processing unit 5 comprises the following steps:

step 100: receiving a measurement signal from the sensors 3 allowing to measure an angle of flexion of the knee 22 of the lower limb 20 of the individual 2;

step 200: determining the value of the angle of flexion of the knee 22 from the measurement signal received in the previous step 100 and determining a swing phase of a walking cycle of the individual from the value of the angle of flexion of the knee;

step 300: generating a control signal only in the swing phase detected in the previous step 200.

The control signal transmitted by the processing unit allows the electrodes 4 to generate electrical stimulation which is a function of the angle of flexion of the knee, and the intensity of the electrical stimulation increasing with the decrease of the angle of flexion of the knee upon re-extension of the knee during the swing phase.

As represented in FIG. 10, the stimulation method for activating at least one muscle involved in raising the foot while an individual using the device according to the invention is walking, comprises the following steps:

step 100a: measuring an angle of flexion of the knee 22 of the individual 2 and determining the swing phase of the walking cycle of the lower limb 20 of the individual 2 from the measured value of the angle of flexion of the knee 22;

step 200a: triggering an electrical stimulation phase of the muscle(s) only during the swing phase detected in the previous step 100a, between a first threshold value and a second threshold value of the angle of flexion of the knee, the intensity of the electrical stimulation being a function of the angle of flexion of the knee 22, and increasing with the decrease of the angle of flexion of the knee upon re-extension of the knee 22 during the swing phase.

According to an additional characteristic of the stimulation method, the stimulation is periodically triggered for n walking cycles of the individual among N considered walking cycles, n being a natural number greater than or equal to 2 and strictly less than N, N being the number of walking cycles.

For example, the control means 53 can trigger a stimulation one walking cycle out of two, so that the user can himself try to raise the foot, before being assisted again by the stimulation controlled by the processing unit 5 generating stimulation profiles. Thereafter, the processing unit can decrease the frequency of the stimulations, and for example trigger a stimulation phase one walking cycle out of three, then one walking cycle out of four, and so on.

The invention claimed is:

1. A stimulation device for activating at least one muscle involved in raising the foot while an individual is walking, comprising:

sensors configured to be placed on a lower limb of the individual and of which measurement signals allow calculating an angle of flexion of the knee corresponding to said lower limb;

electrodes configured to be placed on the muscle(s) to be activated and suitable for electrically stimulating said muscle(s);

one or more processors configured to receive the measurement signals from the sensors, the one or more processors further comprising means for calculating the value of the angle of flexion of the knee from the measurement signals, and means for controlling electrodes connected to the means for calculating and to the electrodes;

characterized in that the means for calculating are configured to determine the swing phase in a walking cycle of the individual;

the means for controlling are configured to:

activate the electrodes only during the swing phase of a walking cycle of the individual so that the electrodes generate electrical stimulation having an intensity as a function of the angle of flexion of the knee, activate the electrodes so that the electrodes generate electrical stimulation with an intensity that increases with the decrease of the angle of flexion of the knee, upon re-extension of the knee during the swing phase.

2. The device according to claim 1, wherein the one or more processors are configured to determine, in the swing phase, an initial-swing sub-phase and a terminal-swing sub-phase, and to activate the electrodes so as that the electrodes generate electrical stimulation with an intensity that increases between a first threshold value and a second threshold value of the angle of flexion of the knee, the first threshold value being in the initial-swing sub-phase, and the second threshold value being reached in the terminal swing sub-phase.

3. The device according to claim 1, wherein the one or more processors are further configured to activate the electrodes such that the electrodes generate electrical stimulation with an intensity that increases between a first threshold value and a second threshold value, the first threshold value being the angle of flexion of the knee of the individual at the beginning of the re-extension of the knee, and the second threshold value being the angle of flexion of the knee of the individual at the end of the re-extension of the knee occurring in a terminal-swing sub-phase of the swing phase.

4. The device according to claim 1, wherein the one or more processors are further configured to activate the electrodes such that the electrodes generate electrical stimulation having an intensity pulse between an initial-swing sub-phase and the beginning of the extension of the knee.

5. The device according to claim 1, wherein the one or more processors are further configured to control the electrodes such that said electrodes generate electrical pulses during the swing phase, the electrical pulses being defined by an amplitude corresponding to the intensity of the current applied to the electrodes, the increase in the intensity of the stimulation during the stimulation phase by said electrodes being carried out by increasing the amplitude.

6. The device according to claim 1, wherein the one or more processors are further configured to control the electrodes so that the intensity of the stimulation increases linearly with the decrease of the angle of flexion upon re-extension of the knee.

7. The device according to claim 1, wherein the one or more processors is configured to control the electrodes so that the intensity of the stimulation increases linearly with the increase of the angle of flexion during the increase of the angle of flexion of the knee of the swing phase.

8. The device according to claim 1, wherein the sensors comprise a first inertial measurement unit and a second inertial measurement unit, and wherein the one or more processors are further configured to calculate the angle of flexion of the knee from the measurements of the inertial measurement units and without measurement of the plantar pressure.

9. The device according to claim 8, wherein the device comprises a first fastener for attaching the first inertial measurement unit to a thigh of the lower limb and a second fastener for attaching the second inertial measurement unit to a tibialis section of said lower limb.

10. One or more processors adapted for a stimulation device for activating at least one muscle involved in raising the foot while an individual is walking, configured to receive measurement signals from sensors, and having:
    means for calculating the value of the angle of flexion of the knee of the lower limb of the individual from the measurement signals and for determining the swing phase in a walking cycle of the individual;
    means for controlling electrodes as a function of the value of the determined angle of flexion of the knee, and connected to the means for calculating;
    characterized in that the means for calculating is configured to generate a control signal for a stimulation phase by said electrodes only during the swing phase of the walking cycle of the individual:
    so that the electrodes generate electrical stimulation the intensity of which is a function of the angle of flexion of the knee,
    so that the electrodes generate electrical stimulation the intensity of which increases with the decrease of the angle of flexion of the knee, upon re-extension of the knee during the swing phase.

11. A computer program product comprising program code instructions recorded on a non-transitory computer medium for performing steps of a processing method for the one or more processors of claim 10,
    wherein said steps comprise:
    receiving measurement signals from the sensors allowing to measure an angle of flexion of the knee of a lower limb of an individual;
    determining the value of the angle of flexion of the knee from the measurement signals and determining the swing phase in a walking cycle of the individual;
    generating a control signal only during the swing phase detected in the previous step, so that:
    the electrodes generate electrical stimulation which is a function of the angle of flexion of the knee and the intensity of which increases with the decrease of the angle of flexion of the knee upon re-extension of the knee during the swing phase;
    when said program is run on a computer.

* * * * *